United States Patent [19]

Stevens et al.

[11] Patent Number: 5,421,727
[45] Date of Patent: Jun. 6, 1995

[54] DENTAL INSTRUMENT WITH MICROWAVE/RF RADIATION AND METHOD OF TREATING A TOOTH

[76] Inventors: Barry H. Stevens, 1015 NW. 105th Ave., Plantation, Fla. 33322; Arye Rosen, 508 Heartwood Rd., Cherry Hill, N.J. 08003; Kevin W. Choi, 345 Camp St., #205, West Yarmouth, Mass. 02673

[21] Appl. No.: 74,652

[22] Filed: Jun. 7, 1993

[51] Int. Cl.⁶ .......................... A61C 5/02; A61C 1/00; A61C 3/00
[52] U.S. Cl. ..................... 433/224; 433/29; 433/32; 433/102
[58] Field of Search ............. 433/27, 29, 32, 102, 433/165, 215, 224; 606/41, 44, 46, 48, 49

[56] References Cited

U.S. PATENT DOCUMENTS

| | | | |
|---|---|---|---|
| 1,713,970 | 5/1929 | Lowry et al. | 606/45 |
| 4,193,408 | 3/1980 | Fujino | 433/27 X |
| 4,302,627 | 11/1981 | Inoue | 433/27 |
| 4,337,038 | 6/1982 | Saito et al. | 433/32 |
| 4,447,206 | 5/1984 | Ushiyama | 433/27 |
| 4,527,560 | 7/1985 | Masreliez | 433/32 X |
| 4,708,647 | 11/1987 | Pippin et al. | 433/32 |
| 5,080,660 | 1/1992 | Buelna | 606/45 |
| 5,207,231 | 5/1993 | Fakhri | 128/787 |

OTHER PUBLICATIONS

"Pathways of the Pulp" Cohen et al. pp. 388–433, 1991.

Primary Examiner—Nicholas D. Lucchesi
Attorney, Agent, or Firm—William H. Meise

[57] ABSTRACT

Dental or endodontic instruments such as drills, files, rasps, broaches, reamers, and the like are arranged to allow radiation of electromagnetic energy into a manmade or natural cavity in the tooth under treatment. The energy may be in the form of microwave or radiofrequency (RF) radiation. The energy raises the temperature of the surrounding tooth material, which tends to disinfect the material as a direct consequence of the temperature. Also, if a disinfectant material is additionally introduced into the tooth cavity, the temperature of the disinfectant material itself may be raised, which enhances its activity. In the particular application to the removal of degenerated pulp, the instrument may be introduced, and electrical or electromagnetic power applied to coagulate the pulp about the instrument, allowing more complete removal of the pulp. The dental instrument may be used with an RF energy delivery system for application of particular amounts of energy per unit time (power). The RF power may be carried through miniature coaxial cables through the dental instrument itself, to enable radiation directly into the interior of the tooth. For this purpose, in some embodiments of the invention the dental instrument includes a portion formed from a dielectric material which allows the energy to pass therethrough. In a particular embodiment, a dental drill includes an antenna near the distal end thereof, a capacitive top cap of which is made from hardened material shaped for removal of tooth material.

8 Claims, 2 Drawing Sheets

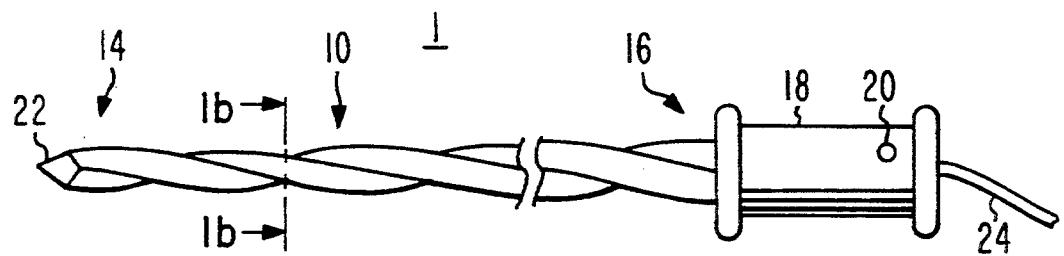
Fig. 1a
Fig. 1b
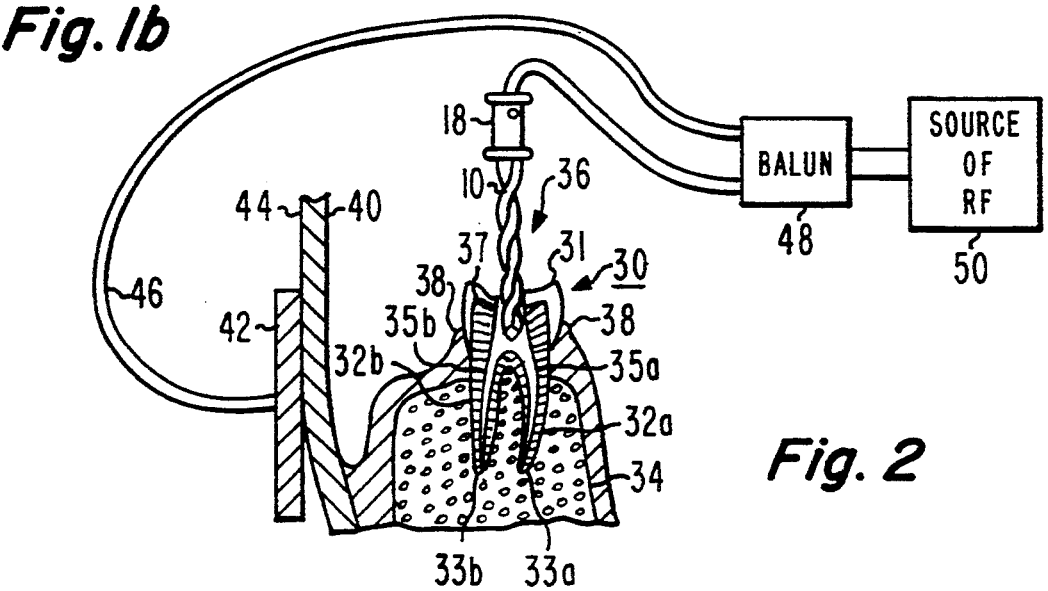
Fig. 2
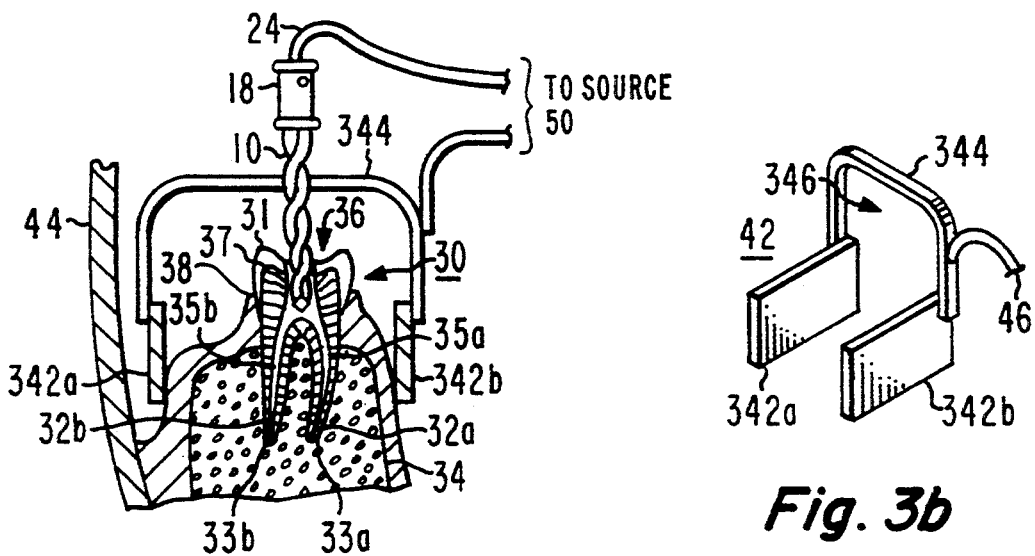
Fig. 3a
Fig. 3b

DENTAL INSTRUMENT WITH MICROWAVE/RF RADIATION AND METHOD OF TREATING A TOOTH

BACKGROUND OF THE INVENTION

This invention relates to dental devices, and more particularly to dental handpieces and/or root-canal (endodontic) instruments, including rotary instruments, arranged for microwave/RF radiation, for aiding in cleaning, disinfecting, shaping and/or sealing the inner confines of a tooth.

Root-canal instruments include files, reamers, rasps, broaches, Hedstrom (H-type) files, and the like. To the uninitiated, many of these instruments have the appearance of a conventional fluted drill bit, but in general the endodontic instruments differ in at least two aspects, namely that they are tapered from distal to proximal ends, and in that the distal end or tip is not shaped for removal of material. Since such instruments are designed for removal of material from their sides rather than from their ends, relatively large bending moments are encountered when they are employed, and the taper provides thickness near the proximal end to resist excessive bending. The shape of the tip is chosen to tend to prevent the possibility of unwanted punctures during procedures. Drills are also used in such procedures. An overview of such devices and their modes of use is given in an article entitled INSTRUMENTS FOR ROOT CANAL PREPARATION, by Cohen & Burns, published at pp 391–409 of Pathways of the Pulp, Mosby Year-Book Inc., 1991. As described therein, many of the instruments are operated manually or hand-driven, to enable the user to maintain a tactile sensation or feel of the contact. Hand-operated quarter-turn rotary and full rotary drivers have been used in conjunction with such instruments. Engine-operated instruments are also used, but care must be taken to prevent perforation and to prevent removal of excessive dental material.

Barbed broaches are used in root-canal procedures to remove intact pulp tissue, by rotating the broach in the pulp to entangle the tissue in the barbs, and removing the entire pulp. When the pulp has degenerated, it has insufficient cohesion to allow removal as a mass.

SUMMARY OF THE INVENTION

According to the invention, dental or endodontic instruments such as drills, files, rasps, broaches, reamers, burrs, and the like are arranged to allow radiation of electromagnetic energy into the tooth under treatment. The energy may be in the form of microwave or radio-frequency (RF) radiation or electrical conduction, which those skilled in the art know are different names for the same type of energy, differing only in that microwave is RF energy lying within particular frequency bands. The energy raises the temperature of the surrounding tooth material, which tends to disinfect the material as a direct consequence of the temperature. Also, if a disinfectant material is introduced into the tooth, the temperature of the disinfectant material itself may be raised, which enhances its activity. In the particular application to the removal of degenerated pulp, the instrument may be introduced, and electromagnetic power applied to coagulate the pulp about the instrument, thereby allowing more complete removal of the pulp, and also allowing simultaneous disinfection. The dental instrument may be used with an RF energy delivery system for application of particular amounts of energy per unit time (power). The RF power may be carried through miniature coaxial cables through the dental instrument itself, to enable radiation directly into the interior of the tooth. For this purpose, in some embodiments of the invention the dental instrument includes a portion which is made from a dielectric material which allows the energy to pass therethrough.

DESCRIPTION OF THE DRAWINGS

FIG. 1a is a side elevation view of a dental instrument according to the invention, including a metallic body and an electrical conductor attached thereto, and FIG. 1b is a cross-section thereof looking in direction 1b—1b;

FIG. 2 is a simplified cross-section of a tooth and the associated lower jaw bone, illustrating the placement of the instrument of FIG. 1 and of an auxiliary electrode, and also illustrating schematically the connections of wires to a source of RF energy;

FIG. 3a is a cross-section similar to that of FIG. 2, illustrating the shape and placement of a bipartite electrode, and FIG. 3b is a perspective or isometric view of the bipartite electrode of FIG. 3a;

DESCRIPTION OF THE INVENTION

Figure 4:
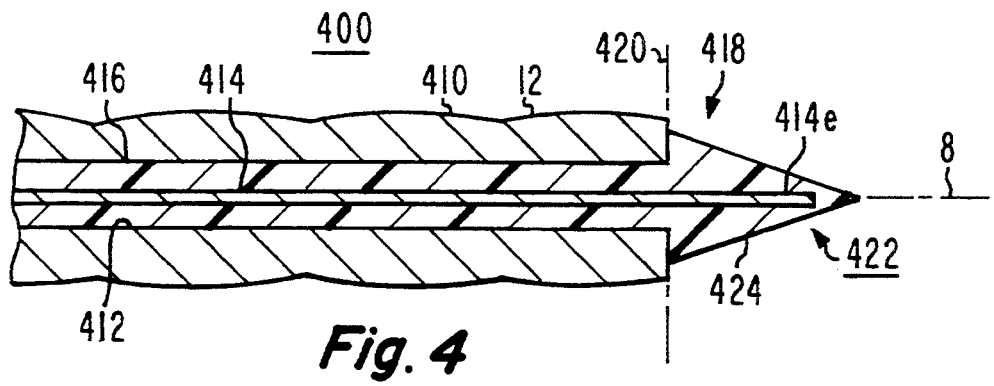
FIG. 4 is a longitudinal cross-section of a distal portion of another instrument according to the invention, in which a coaxial transmission-line extends axially therethrough, and which has an antenna at the distal end thereof.

FIG. 1a illustrates a dental instrument 1 including an elongated polygonal-cross-section metallic body 10, in this case square as illustrated in FIG. 1b, twisted about its longitudinal axis to form the vertices of the square into a plurality of helical cutting or material removal edges, one of which is designated 12. Body 10 defines a distal end 14 and a proximal end 16 which is attached to a plastic or other dielectric handle 18. Handle 18 includes a transverse aperture 20 for ligation of the instrument, if necessary. As illustrated, body 10 is slightly tapered, and has a tapered end 22 at its distal end. According to an aspect of the invention, an elongated electrically conductive wire 24 is affixed within handle 18 to the proximal end of body 10, whereby a path for the flow of electric current exists between wire 24 and body 10. Wire 10 is insulated on its exterior to prevent contact of the conductive portion to the patient or the doctor during procedures.

FIG. 2 is a simplified cross-section of a portion of the lower jaw of a patient, illustrating the location of body 10 of instrument 1 of FIG. 1a within a tooth cavity, and the location of an additional or auxiliary electrode exterior to the cheek. Elements of FIG. 2 corresponding to those of FIG. 1a are designated by like reference numerals. As illustrated in FIG. 2, a tooth 30 includes a bipartite root 32a, 32b imbedded in the jaw bone and periodontium tissue 34. A layer of enamel 31 of tooth 30 overlies a dentin structure 37. Within tooth 30, a bipartite root canal 35 extends through the roots to their respective apexes or apices 33a, 33b. Tooth 30 defines a natural or man-made cavity 36 which extends through the enamel toward the apexes 33a, 33b of roots 32a and 32b, respectively. Gum or gingival tissue designated 38 butts against both sides of tooth 30, and extends over jaw material 34, and, together with other tissue, eventually meets the tissue, designated 40, of the adjacent cheek of the patient.

According to an aspect of the invention, an electrically conductive, flat auxiliary electrode, illustrated in cross-section in FIG. 3a as a rectangular structure 42, is maintained in contact with exterior surface 44 of cheek tissue 40. A wire 46 attached to electrode 40 allows application of RF energy to the electrode. Wires 24 and 46 are coupled to a source of RF energy 50 by way of a balun apparatus 48, if appropriate. "Balun" is a conventional term for a BALanced-to-UNbalanced transition, which as known to those skilled in the art may be used to convert the electric field configurations of energy flowing (in either direction) between balanced and unbalanced transmission lines. Also, while the term "transmission line" ordinarily means an elongated pair of electrical conductors configured with a constant cross-sectional shape so as to provide a constant impedance at all transverse points, in the present context it also includes a pair of wires such as wires 24 and 46, which are spaced from each other by different distances at different points across their length. Such non-constant impedance transmission lines are quite effective when their length is less than one-tenth wavelength. Source 50 of RF energy may be conventional, and may include controls and/or monitors for power level. In the arrangement of FIG. 2, body 10 of the instrument, electrode 42, and the intervening tissue region, constitute a load for the RF signal source, which couples energy thereto. Source 50 may also include tuning adjustments for maximizing power transfer to the particular load represented by instrument 1 in conjunction with electrode 42 and the tissue. It should be noted that the amount of RF or microwave energy per unit of time is termed power, and that the terms "energy" and "power" are often used interchangeably in descriptions of transmission lines and antennas. While the terms "RF" and "microwave" are used herein, the invention can also be used at frequencies which are so low that conventional antenna radiation is not large, but at which near-field effects cause electrical conduction in the region being treated.

In operation of the arrangement of FIG. 2, source 50 couples electromagnetic (or conductive) energy to the region between instrument body 10 and electrode 42, including the region adjacent body 10 of instrument 1. Those skilled in the art know that the field configuration resulting from small-diameter body 10 in conjunction with large-area electrode 42 is relatively concentrated near body 10. Application of a given amount of power, therefore, will tend to increase the temperature of tissue near body 10 more than tissue near electrode 42. Thus, the amount of power may be selected to satisfy the requirements near body 10, without fear of damaging other, more remote tissue, such as that adjacent large-area electrode 42. The amount of power may be selected to slightly warm the region to enhance the efficacy of a disinfectant liquid or to improve blood flow, to heat sufficiently to disinfect in the absence of a disinfectant liquid, or to kill tissue or coagulate it into a cohesive mass, or to cause a glazing of tooth structure aimed at decreasing its permeability to fluids or microorganisms, or to melt sealing material evenly in the root canal.

FIG. 3a is a cross-section similar to that of FIG. 2, and elements thereof corresponding to those of FIG. 2 are designated by the same reference numerals. FIG. 3b is a perspective or isometric view of the electrode of FIG. 3a. Electrode 42 is bipartite, and it is located inside the mouth during use, as illustrated in FIG. 3a. Referring to FIG. 3b, electrode 42 includes two parts or portions, illustrated as conductive flat plates 342a and 342b. Plates 342a and 342b may be rigid and shaped to fit various portions of the mouth, or they may be flexible, so that they may be shaped during fitting to the patient. As also illustrated in FIGS. 3a and 3b, electrode plates 342a and 342b are held together by a flexible or elastic conductive spring 344, which is shaped with a large loop 346 which is dimensioned to clear the upper surfaces of the tooth or row of teeth with which it is associated when in use. Spring 344 is tensioned by the spreading of electrode plates 342a and 342b necessary to place them in position straddling the tooth, so it supplies force urging the electrodes toward each other, which tends to hold the electrodes in the desired location. Connecting wire 46 is affixed to spring 344, but it could as well be affixed to either of the electrodes, because they are all at the same electrical potential. The electrode structure of FIGS. 3a and 3b is advantageous over that of FIG. 2 because the electrodes are closer to body 10 of the instrument, which concentrates the fields near the region being treated, and also because the heating effect tends to be more uniform than when one electrode is used, because the field structure is evenly divided between electrodes 342a and 342b of the pair.

FIG. 4 is a simplified cross-section of the distal end of a dental instrument 400 including a conductive metallic body 410, through which a bore 412 is formed. Within bore 412, an elongated electrical conductor 414 extends parallel to axis 8, spaced away from the metallic walls of bore 412 by a tube 416 of dielectric material, which may be polytetrafluoroethane (TEFLON), or any of a number of other known low-loss dielectric materials. This structure forms an unbalanced transmission line in which electromagnetic energy is carried in the region between center conductor 414 and an outer conductor defined by the inside surface of bore 412. At the distal end 418 of instrument body 410, the metallic portion of the body is truncated at a plane 420. According to the invention, a portion designated 414e of center conductor 414 extends to the right past plane 420, to thereby form an electromagnetic radiating antenna designated 422. That portion of center conductor 414 extending past the truncated end of instrument body 410 is supported and protected by an extended window region, designated 424, of the same dielectric material which occupies the bore. Extended dielectric region 424 has a roughly conical shape, corresponding to the non-penetrating shape desired for files, rasps, broaches, reamers and the like. The resilient nature of the polytetrafluoroethane dielectric may tend to provide further protection against puncture.

Those skilled in the art of balanced and unbalanced antennas know that what is commonly termed an "antenna" in the case of an unbalanced antenna is often just a portion of the antenna, the "ground" portion not being obvious. Antenna 422 of FIG. 4 is a form of unbalanced antenna, in which the electrical currents flowing on a portion of the exterior of the surface of body 410 coact with similar currents flowing on center conductor extension 414e to effect the antenna radiation.

Figure 5:
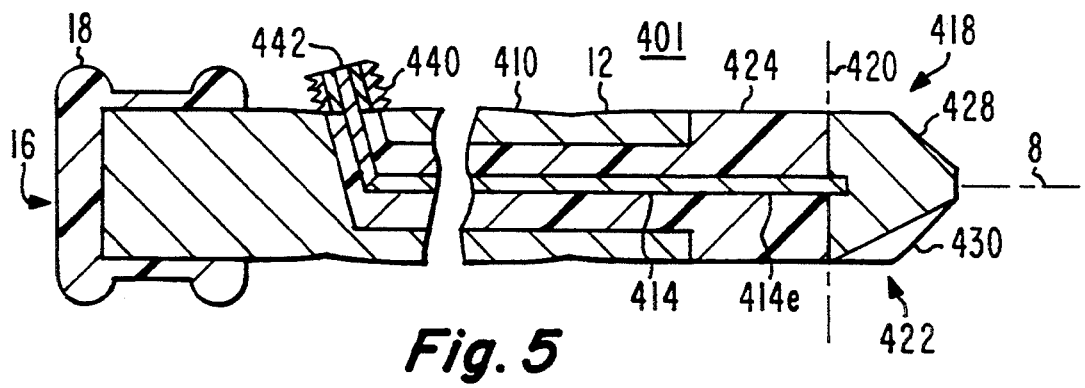
FIG. 5 is a longitudinal cross-section similar to that of FIG. 4, in which the instrument is a drill, and the antenna includes a capacitive top cap which is configured for removal of tooth material.

According to another aspect of the invention, a dental drill includes a coaxial transmission line and an antenna as described in conjunction with FIG. 4, but also includes a hard or metallic end which is configured for drilling, and which also is connected to the distal end of the center conductor of the transmission line, for acting as a capacitive "top cap", to thereby tend to linearize the current distribution of the antenna, to enhance the radiation efficiency. FIG. 5 is similar to FIG. 4, and corresponding elements are designated by like reference numerals. In FIG. 5, antenna 422 of instrument 401 includes center conductor extension 414e and an electrically conductive drill bit end 428 which is electrically connected thereto. Drill bit end 428 may be hardened, if desired, and in any case includes an exterior surface 430 shaped for removal of tooth material.

At the proximal end of instrument 401 of FIG. 5, a coaxial electromagnetic connector 440 is affixed to instrument body 410, and includes an outer conductor body in electrical contact with body 410, and an inner conductor which is insulated from the outer conductor, and which is connected to elongated conductor wire 414.

Figure 6:
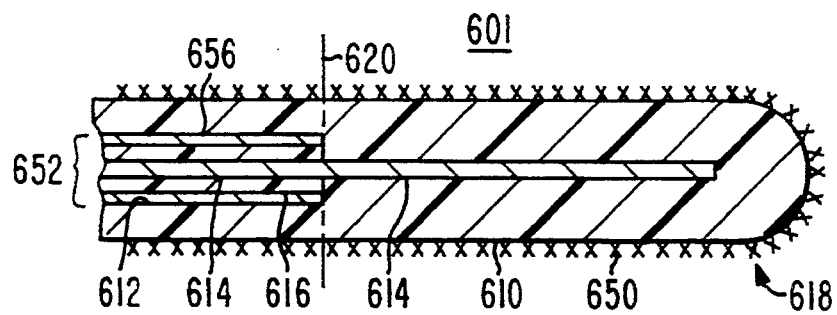
FIG. 6 is a longitudinal cross-section of the distal end of an abrasive dental instrument including an antenna according to the invention.

FIG. 6 is a longitudinal cross-section of a the distal end of a diamond-coated abrasive burr according to an aspect of the invention. In FIG. 6, burr 601 includes a body 610 defining a distal end 618. Body 610 is made from a dielectric material, and diamond grit, illustrated by "Xs" 650, is attached to the outer surface of body 610 by adhesive, or by impregnation of the dielectric in a gel form before curing to a hard form. As illustrated in FIG. 6, a coaxial transmission line or cable 652 is fitted into a bore 612 within body 610. Coaxial cable 652 includes a center conductor 614 spaced by a dielectric insulating material 616 from an outer conductor 656. The outer conductor may be made from a braided conductive material to enhance flexibility. A distal portion 614a of center conductor 614 extends distally beyond a plane 620, to form an antenna as described above in conjunction with FIG. 4.

Figure 7:
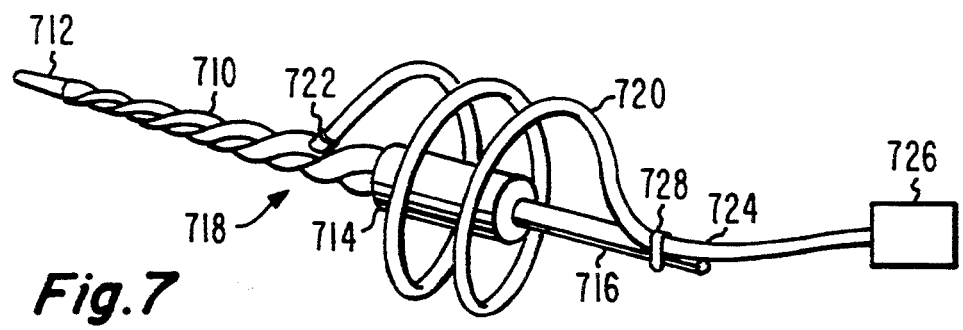
FIG. 7 is a perspective or isometric view of a rotatable dental tool with an arrangement for conveying RF/microwave energy to the tool.

FIG. 7 illustrates a metallic dental instrument or tool 710 with a dielectric window 712 near its distal end, and which contains a coaxial transmission line (not visible in FIG. 7), as described above, extending distally from a connector or terminal 722 at a transverse location designated 718 to an antenna (not visible in FIG. 7) located within body 710, adjacent window 712. Instrument 6 is supported at its proximal end by a reciprocal-rotary (limited rotational travel) drive apparatus illustrated as a cylinder 714, which is supported by a support shaft 716. RF/microwave energy may be coupled to the coaxial transmission line within instrument 710 by means of a flexible coaxial transmission line designated 20, which makes loops about drive apparatus 714. Flexible coaxial transmission lines are well known in the art, and are generally made with a foil or braided outer conductor, or both, and with a stranded center conductor. The center conductor (not visible in FIG. 7) of flexible coaxial cable 720 is coupled by connector 722 to the center conductor (also not visible in FIG. 7) of the coaxial cable extending within tool body 710, and the outer conductor of the flexible coaxial cable 720 is also connected thereby to the metallic body of tool 710, to provide a continuous path for the flow of RF/microwave energy. One end of the loop of flexible coaxial cable 720 is held in place by a clip 728 which holds it to support shaft 716. In operation, the area of the loop defined by coaxial cable 720 becomes greater and less, as drive apparatus 714 reciprocates tool 710, and RF/microwave energy may be applied from a source 726 through cable 720 to tool 710, for radiation by the antenna within through window 712.

Other embodiments of the invention will be apparent to those skilled in the art. For example, electrode plates 42 of FIG. 2 or 342a,b of FIGS. 3a,b may be made of a nonconductive base material covered or coated with a conductive layer or film. While a single conductive spring is illustrated as holding electrodes 342a and 342b in FIGS. 3a and 3b, two or more such springs may be used, one at each end of the electrodes, to provide improved support. Ordinary linear antennas (monopoles or dipoles) have been described, but any type of antenna may be used, as for example single or multiturn loops, unloaded or loaded with magnetically permeable material, frequency-independent antennas, arrays and the like.

What is claimed is:

1. A dental instrument, comprising:
   an elongated body defining a longitudinal axis, a distal end, a proximal end, and a material removal outer surface lying between said distal and proximal ends, said body also defining a longitudinal bore portion, said body including at least a window portion lying near said distal end, which window portion includes a path of dielectric material extending from said longitudinal bore portion to said outer surface; and
   an elongated electrical conductor extending within said bore through at least a portion of said window portion, and from said window portion to a location more proximal than said window portion, and extending from said location more proximal than said window portion to a location outside said body material removal outer surface whereby an RF/microwave connection can be made thereto;
   wherein the cross-sectional shape of said body in a plane transverse to said longitudinal axis is a polygon defining vertices.

2. An instrument according to claim 4, wherein said body is composed of electrically conductive material, and further comprising:
   a dielectric tube lying within said bore, said dielectric tube surrounding said elongated electrical conductor, whereby said elongated electrical conductor, said dielectric tube and said electrically conductive body together form a coaxial transmission line extending longitudinally through said body from said location more proximal than said window portion to said window portion.

3. An instrument according to claim 1, wherein said polygon shape is angularly displaced about said longitudinal axis, thereby forming said vertices into helices.

4. A dental tool, comprising:
   an elongated, flexible body of material defining a longitudinal axis, an outer surface adapted for the removal of dental material, and proximal and distal ends, said body also defining a longitudinal bore extending parallel to said longitudinal axis from said proximal end toward said distal end, said body including at least a window portion of electrically nonconductive dielectric material at a location remote from said proximal end;

an elongated dielectric tube lying within said bore; and an elongated electrical conductor lying within said tube, said conductor defining a distal end located adjacent said window portion;

wherein said body is of a hard material and further comprises a polygonal cross-section, helically disposed about said longitudinal axis to thereby form flutes, edges of which constitute said outer surface adapted for the removal of dental material.

5. A dental tool according to claim 4, wherein said material of said flexible body is metallic.

6. A dental tool, comprising:

an elongated, flexible body of material defining a longitudinal axis, an outer surface adapted for the removal of dental material, and proximal and distal ends, said body also defining a longitudinal bore extending parallel to said longitudinal axis from said proximal end toward said distal end, said body including at least a window portion of electrically nonconductive dielectric material at a location remote from said proximal end;

an elongated dielectric tube lying within said bore; and an elongated electrical conductor lying within said tube, said conductor defining a distal end located adjacent said at least a window portion wherein said outer surface of said body, which is adapted for the removal of dental material, comprises helically disposed fluted edges.

7. A method for treating a tooth defining a cavity therein, comprising the steps of:

placing an electrode adjacent said tooth;

inserting into said cavity an instrument including a metallic portion; and applying RF energy to said electrode and said metallic portion of said instrument;

wherein said step of placing an electrode adjacent said tooth includes the step of fitting a pair of electrodes over said tooth, so that said tooth is effectively placed between said pair of electrodes.

8. A method according to claim 7, wherein said step of applying said RF energy includes the step of propagating said energy by means of a pair of elongated, electrically conductive metallic wires.

* * * * *